US00PP32955P2

(12) United States Plant Patent
Van Swieten

(10) Patent No.: US PP32,955 P2
(45) Date of Patent: Apr. 6, 2021

(54) ***PHALAENOPSIS* ORCHID PLANT NAMED 'PHALHUCAR'**

(50) Latin Name: ***Phalaenopsis* hybrid**
Varietal Denomination: PHALHUCAR

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/904,744

(22) Filed: Jun. 18, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALHUCAR', particularly characterized by small, greenish-yellow, dotted flowers with reddish-purple lips, lightly scented flowers, a large bump and ridge on the apical lobe of the lip, flower longevity on the plant of about 21 weeks, and is propagated by meristem tissue culture, is disclosed.

3 Drawing Sheets

Genus and species: *Phalaenopsis* hybrid.
Variety denomination: 'PHALHUCAR'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHUCAR'.

The new *Phalaenopsis* plant is a product of a planned breeding program conducted by the inventor in Bleiswijk, the Netherlands. The objective of this breeding program was to create a new *Phalaenopsis* plant with numerous attractive and small, greenish-yellow, dotted flowers with reddish-purple lips, suitable for potted plant production.

The new *Phalaenopsis* plant 'PHALHUCAR' is a result of cross-pollination made by the inventor in December 2011 in Bleiswijk, the Netherlands, of the proprietary female, or seed parent, *Phalaenopsis* hybrid '01-4151' (unpatented) with the proprietary male, or pollen parent, *Phalaenopsis* hybrid '01-4153' (unpatented).

The new *Phalaenopsis* was selected by the inventor as a single plant within the progeny of the stated cross-pollination in a controlled greenhouse in Bleiswijk, the Netherlands, in September 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019 (Application no. 2019/1000), by Applicant who obtained the subject matter disclosed directly from the inventor. 'PHALHUCAR' has not been made publicly available or sold anywhere in the world prior to the effective filing date of this application with the exception of sales or disclosures made one year or less before the effective filing date of this claimed invention by Applicant who obtained 'PHALHUCAR' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHUCAR' as a new and distinct variety of *Phalaenopsis* plant:

1) Small, greenish-yellow, dotted flowers with reddish-purple lips;
2) Lightly scented flowers;
3) Large bump and ridge on the apical lobe of the lip; and
4) Flower longevity on the plant of about 21 weeks.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2020. Colors in the photographs may differ from the color values cited in the detailed botanical description, which accurately describe the actual colors of the new variety.

DESCRIPTION OF THE NEW VARIETY

Figure 1:
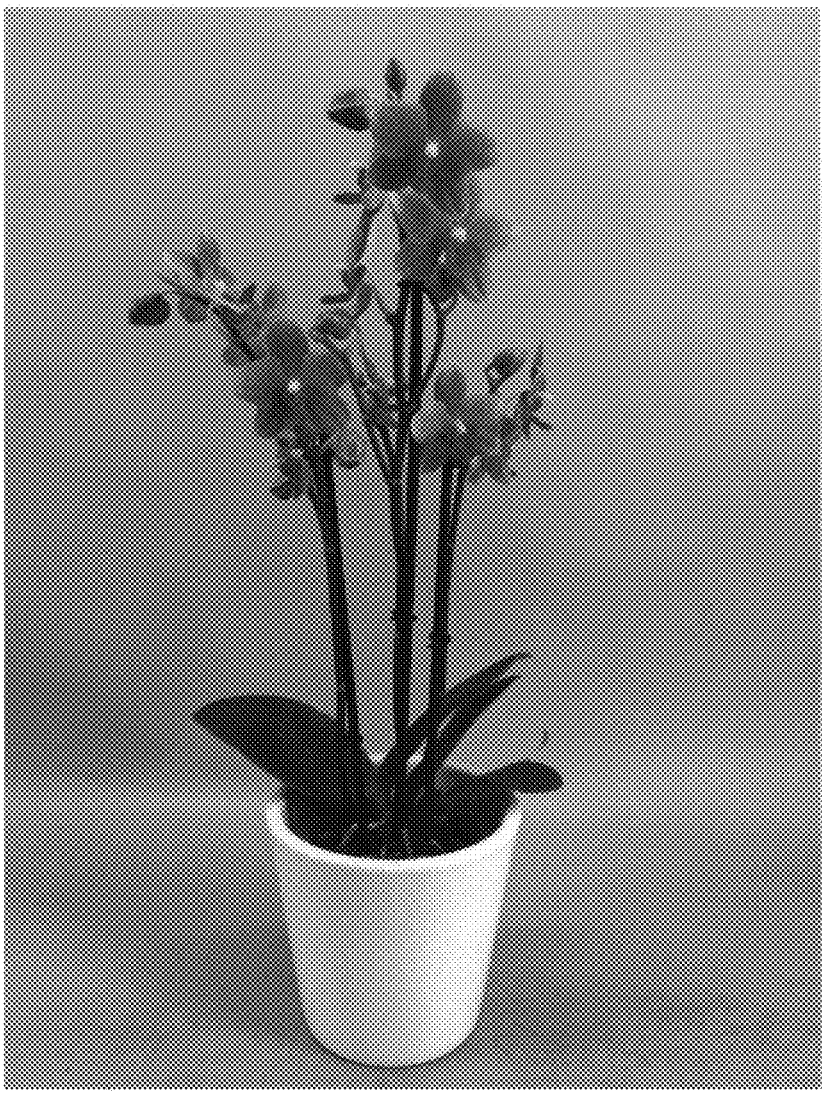
FIG. 1 shows the overall plant habit, including blooms, buds, and foliage of 'PHALHUCAR'.
Figure 2:
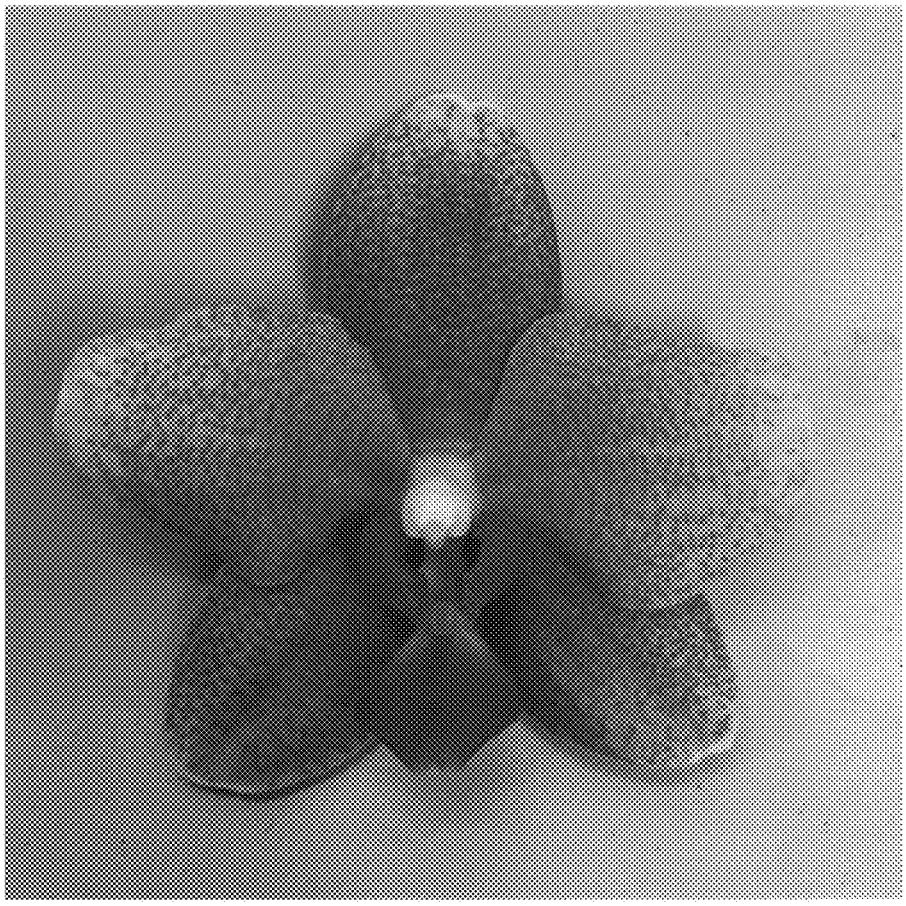
FIG. 2 shows a close-up of a flower of 'PHALHUCAR'.
Figure 3:
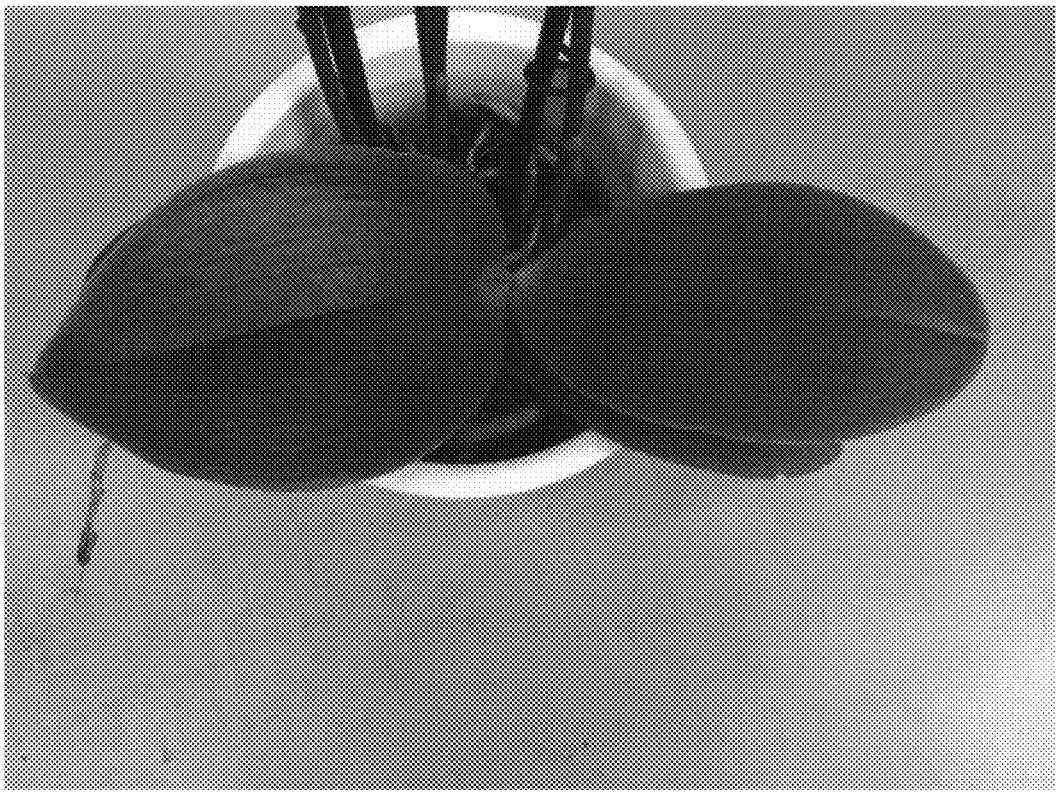
FIG. 3 shows an overhead view of the leaves of 'PHALHUCAR'.

The following detailed description sets forth the distinctive characteristics of 'PHALHUCAR'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHUCAR'.

Parentage:

*Female parent*.—*Phalaenopsis* cultivar '01-4151' (unpatented).

*Male parent*.—*Phalaenopsis* cultivar '01-4153' (unpatented).

Propagation:

*Type*.—Meristem tissue culture.

Roots:

*Root description*.—Greyed-green (something between RHS 190B and 190C) colored roots with branching lateral roots having yellow-green (RHS 145C) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 35.0 cm to 40.0 cm.

*Width* (*measured from leaf tips*).—About 22.0 cm to 25.0 cm.

*Vigor*.—Strong.

Leaves:

*Mature leaves*.—Quantity per plant: 7 to 8 leaves are produced before flowering. Length (fully expanded): 12.0 cm to 14.0 cm. Width: 7.0 cm to 8.0 cm. Position of the broadest part of the leaf: At the middle. Shape: Oblong. Base shape: Slightly to moderately elongated. Apex: Obtuse asymmetric. Leaf blade angle with the petiole (measured from the horizontal position): Between 20 degrees and 35 degrees. Leaf margin: Entire. Color: Upper surface: RHS 146A. Lower surface: RHS 146B. Texture (both upper and lower surfaces): Smooth. Thickness: 2.3 mm to 2.6 mm. Variegation: Absent. Venation: Pattern: Parallel. Color of the midvein: Upper surface: RHS 146A. Lower surface: RHS 146B.

Peduncle:

*Quantity per plant*.—2 to 4.

*Number of flowers per peduncle*.—9 to 13.

*Length*.—35.0 cm to 40.0 cm.

*Diameter*.—4.5 mm to 4.9 mm.

*Strength*.—Strong.

*Aspect*.—Upright to slightly pendent.

*Texture*.—Smooth.

*Color*.—Green (RHS 146A) with a hint of brown (RHS 200B).

*Internode length*.—3.5 cm to 4.5 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 190.0 mm to 220.0 mm.

*Flowering time*.—First flowers can be expected 10 to 11 months after planting in a 12-cm pot.

*Flower*.—Height: 53.0 mm to 58.0 mm. Diameter: 55.0 mm to 60.0 mm. Depth of lip: 18.0 mm to 20.0 mm.

*Flower longevity*.—On the plant: 20 to 22 weeks.

*Flower shape*.—Flat.

*Fragrance*.—Present (light scent).

*Flower bud*.—Average size: Medium. Length: 19.0 mm to 21.0 mm. Width: 15.0 mm to 17.0 mm. Shape: Egg shaped. Color: Greenish-yellow (RHS 151A) with small red region and stripes (RHS 184B).

*Petals*.—Arrangement: Open/free. Shape: Semi-circular. Apex: Rounded asymmetric. Margin: One margin of the petal is curled backwards. Length (from base to tip): 27.0 mm to 29.0 mm. Width: 24.0 mm to 26.0 mm. Position of the broadest part of the petal: Toward the base. Color (when fully opened): Upper surface: Basic color: Greenish-yellow (RHS 2A). Over color: Reddish-purple (RHS N78A) at the base; red shade (RHS 181A). Lower surface: Basic color: Greenish-yellow (RHS 2B). Over color: Very light purple (RHS 76B) at the base; diluting red stripes (RHS 182A). Number of spots, dots, and stripes on the petals (upper surface): Very many, very small dots. Color of spots, dots, and stripes on the petals (upper surface): RHS 185A. Density of netting of the petals (upper surface): None. Color of the netting (upper surface): None.

*Dorsal sepal*.—Shape: Elliptic. Apex: Emarginated symmetric. Margin: Entire. Length (from base to tip): 29.0 mm to 31.0 mm. Width: 21.0 mm to 23.0 mm. Position of the broadest part of the dorsal sepals: At the middle. Color (when fully opened): Upper surface: Basic color: Greenish-yellow (RHS 2A). Over color: At the base hint of reddish-purple (RHS N78A) and red (RHS 59B). Lower surface: Basic color: Yellow (RHS 153D). Over color: Hint of very light purple (something in between RHS 76B and 76C) at the base; red stripes (RHS 182A). Number of spots, dots, and stripes on the dorsal sepals (upper surface): Very many, very small dots. Color of spots, dots, and stripes on the dorsal sepals (upper surface): RHS 185A. Density of netting of the dorsal sepals (upper surface): None. Color of the netting (upper surface): None.

*Lateral sepals*.—Shape: Ovate. Apex: Cuspidate asymmetric. Margin: Entire. Length (from base to tip): 29.0 mm to 31.0 mm. Width: 20.0 mm to 22.0 mm. Position of the broadest part of the lateral sepals: Toward the base. Color (when fully opened): Upper surface: Basic color: Greenish-yellow (RHS 2A). Over color: Hint of reddish-purple (RHS N78A) and red (RHS 59B) at the base; red shade (RHS 181B). Lower surface: Basic color: Yellow (RHS 153D). Over color: Hint of very light purple (RHS 76C) at the base; dots (something in between RHS 182C and 182D). Number of spots, dots, and stripes on the lateral sepals (upper surface): Very many, very small dots. Color of spots, dots, and stripes on the lateral sepals (upper surface): RHS 185A. Density of netting of the lateral sepals (upper surface): None. Color of the netting (upper surface): None.

*Labellum* (*lip*).—Whiskers: Absent. Length of whiskers: Not applicable. Color of whiskers: Not applicable. Pubescence on the lip: Absent.

*Lateral lobe*.—Shape: Type I (as described in the International Union for the Protection of New Varieties of Plants (UPOV) Test Guidelines for *Phalaenopsis*); ligulate. Margin: Slightly undulated. Length: 8.0 mm to 10.0 mm. Width: 3.0 mm to 5.0 mm. Color: Upper surface: Slightly white (RHS NN155C) at the base; purplish-red (RHS N79C) toward margins and tip. Lower surface: White (RHS NN155C) at the base; reddish-purple (RHS N78A) toward the margin. Number of spots and stripes on the lateral lobe: Medium to many. Color of spots and stripes on the lateral lobe: RHS 71A. Density of netting of the lateral lobe: None. Color of the netting: None.

*Apical lobe*.—Shape: Rhombic. Margin: Entire. Length: 15.0 mm to 17.0 mm. Width: 11.0 mm to 13.0 mm. Color: Upper surface: Reddish-purple (RHS N78A); red (RHS 185A) toward the wings; red middle vein (RHS 183B). Lower surface: Light yellow (RHS 160B) at the base; slightly red wings (RHS 185A); light purple (RHS 76A) at the middle and reddish-purple (RHS N78A) toward margins. Number of spots and stripes on the apical lobe: None. Color of spots and stripes on the apical lobe: None. Density of netting of the apical lobe: None. Color of the netting: None. Bump and ridge: Large.

*Callus*.—Average size: Very small. Height: 4.0 mm to 5.0 mm. Length: 3.0 mm to 4.0 mm. Width: 2.0 mm to 3.0 mm. Color: Light greenish-yellow (RHS 8C) at the base and purplish-red (RHS 186A) toward the tip.

Reproductive organs:

*Column*.—Length: 8.0 mm to 10.0 mm. Diameter: 3.8 mm to 4.2 mm. Color: Very light purple (RHS 76B to RHS 76C) toward the tip.

*Pollinia*.—Quantity: 2. Diameter: 0.8 mm to 1.0 mm. Color: Orange-yellow (RHS 23A).

*Ovary*.—Length: 11.0 mm to 13.0 mm. Diameter: 2.1 mm to 2.3 mm.

*Pedicel*.—Length: 37.0 mm to 39.0 mm. Diameter: 2.5 mm to 2.7 mm. Texture: Smooth. Color: Light yellow-green (RHS 145C) and lighter yellow-green (RHS 145D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALHUCAR', cultivar '01-4151' (unpatented), is no longer in existence, therefore a meaningful comparison cannot be made.

The male parent plant of 'PHALHUCAR', cultivar '01-4153' (unpatented), is no longer in existence, therefore a meaningful comparison cannot be made.

'PHALHUCAR' is most similar to the commercial *Phalaenopsis* plants named 'PHALGASCIJ' (U.S. Plant Pat. No. 32,286) and 'PHALVILMYK' (U.S. Plant Pat. No. 32,008). 'PHALHUCAR' differs from the commercial variety 'PHALGASCIJ' in that 'PHALHUCAR' has ligulate lateral lobes, rhombic apical lobes, rounded petal apexes, and no whiskers, whereas 'PHALGASCIJ' has oblong lateral lobes, elliptic apical lobes, emarginated petal apexes, and whiskers. Additionally, 'PHALHUCAR' has smaller flowers than 'PHALGASCIJ'.

'PHALHUCAR' differs from the commercial variety 'PHALVILMYK' in that 'PHALHUCAR' has ligulate lateral lobes, rounded petal apexes, light greenish-yellow and purplish-red calluses, and no whiskers, whereas 'PHALVILMYK' has weakly spatulate lateral lobes, emarginated petal apexes, yellow, flecked calluses, and whiskers. Additionally, 'PHALHUCAR' has smaller flowers than 'PHALVILMYK'.

I claim:

1. A new and distinct variety of *Phalaenopsis* plant named 'PHALHUCAR', substantially as described and illustrated herein.

* * * * *